(12) United States Patent
Rivard et al.

(10) Patent No.: US 12,329,978 B2
(45) Date of Patent: *Jun. 17, 2025

(54) IMPLANTABLE MEDICAL LEADS AND LEAD EXTENSIONS HAVING AN ENCAPSULATION BAND

(71) Applicant: MEDTRONIC, INC., Minneapolis, MN (US)

(72) Inventors: Adam J. Rivard, Blaine, MN (US); Mary Bengtson, Ham Lake, MN (US); Stephen L. Bolea, Watertown, MN (US); Justin M. Claus, Fridley, MN (US); Ryan R. Davis, Plymouth, MN (US); Scott M. Hanson, Savage, MN (US); Sean P. Skubitz, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 250 days.

This patent is subject to a terminal disclaimer.

(21) Appl. No.: 17/744,780

(22) Filed: May 16, 2022

(65) Prior Publication Data
US 2022/0273955 A1    Sep. 1, 2022

Related U.S. Application Data

(63) Continuation of application No. 16/396,389, filed on Apr. 26, 2019, now Pat. No. 11,331,502.

(51) Int. Cl.
*A61N 1/375* (2006.01)
*A61L 31/10* (2006.01)
(Continued)

(52) U.S. Cl.
CPC ............ *A61N 1/3752* (2013.01); *A61L 31/10* (2013.01); *A61N 1/0529* (2013.01); *A61N 1/08* (2013.01);
(Continued)

(58) Field of Classification Search
CPC ...... A61N 1/0529; A61N 1/0551; A61N 1/08; A61N 1/36125; A61N 1/3752; A61N 1/3758; A61L 31/10
See application file for complete search history.

(56) References Cited

U.S. PATENT DOCUMENTS

| | | |
|---|---|---|
| 4,922,607 A | 5/1990 | Doan |
| 4,944,088 A | 7/1990 | Doan |

(Continued)

OTHER PUBLICATIONS

Prosecution History from U.S. Appl. No. 16/396,389, now issued U.S. Pat. No. 11,331,502, dated May 12, 2021 through Apr. 22, 2022, 44 pp.

*Primary Examiner* — Christopher A Flory
(74) *Attorney, Agent, or Firm* — Shumaker & Sieffert, P.A.

(57) ABSTRACT

Implantable medical leads and/or lead extensions include a band that encapsulates a portion of conductors of the lead and/or lead extension. The band may be reflowed in order to provide the encapsulation of the conductors. The band may further be used to create a seal together with the surrounding lead body and an additional object such as a stiffener rod, stylet tube, and/or molding stylet, to allow a proximal area of a lumen of the lead body to be injection molded while prevent the injection molding material from proceeding past the band. When a stiffener rod is present in a proximal area of the lead and/or lead extension, additional stiffness is provided to the lead body to resist buckling of the lead body during insertion of the proximal end. The band may be bonded to the stiffener rod to fix the position of the stiffener rod relative to the conductors.

24 Claims, 17 Drawing Sheets

(51) Int. Cl.
*A61N 1/05* (2006.01)
*A61N 1/08* (2006.01)
*A61N 1/36* (2006.01)

(52) U.S. Cl.
CPC ........ *A61N 1/0551* (2013.01); *A61N 1/36125* (2013.01); *A61N 1/3758* (2013.01)

(56) References Cited

U.S. PATENT DOCUMENTS

| | | |
|---|---|---|
| 5,304,219 A | 4/1994 | Chernoff |
| 5,324,321 A | 6/1994 | Pohndorf |
| 5,358,516 A | 10/1994 | Myers et al. |
| 5,366,494 A | 11/1994 | Holleman |
| 5,476,493 A | 12/1995 | Muff |
| 5,489,269 A | 2/1996 | Aldrich |
| 5,545,203 A | 8/1996 | Doan |
| 5,657,704 A | 8/1997 | Schueler |
| 5,766,042 A | 6/1998 | Ries |
| 6,096,069 A | 8/2000 | Bischoff |
| 6,567,704 B2 | 5/2003 | Sundquist et al. |
| 7,766,868 B2 | 5/2010 | Goode |
| 7,917,229 B2 | 3/2011 | Zarembo et al. |
| 8,170,691 B2 | 5/2012 | Eckerdal |
| 8,391,982 B2 | 3/2013 | Barker |
| 8,543,222 B1 | 9/2013 | Sochor |
| 8,577,476 B2 | 11/2013 | Henricks et al. |
| 8,583,258 B2 | 11/2013 | Maxfield |
| 8,588,933 B2 | 11/2013 | Floyd et al. |
| 8,911,265 B2 | 12/2014 | Maio et al. |
| 9,050,454 B2 | 6/2015 | Hendricks et al. |
| 9,333,341 B2 | 5/2016 | Sommer |
| 9,757,555 B2 | 9/2017 | Novotny et al. |
| 10,071,238 B2 | 9/2018 | Ollivier |
| 11,331,502 B2 | 5/2022 | Bolea et al. |
| 2002/0077685 A1 | 6/2002 | Sundquist |
| 2004/0215300 A1 | 10/2004 | Verness |
| 2008/0046059 A1 | 2/2008 | Zarembo |
| 2010/0137928 A1 | 6/2010 | Duncan |
| 2010/0331942 A1 | 12/2010 | Cholette |
| 2011/0009934 A1 | 1/2011 | Conger |
| 2011/0301678 A1 | 12/2011 | Alexander |
| 2012/0041529 A1 | 2/2012 | Olsen |
| 2012/0046722 A1 | 2/2012 | Olsen |
| 2012/0053664 A1 | 3/2012 | Hegland |
| 2013/0025122 A1 | 1/2013 | Conger |
| 2013/0030509 A1 | 1/2013 | Conger |
| 2013/0267127 A1 | 10/2013 | Di Maio |
| 2014/0180252 A1 | 6/2014 | Gabriel |
| 2015/0073432 A1 | 3/2015 | Barker |
| 2015/0209579 A1 | 7/2015 | Olsen |
| 2015/0374978 A1 | 12/2015 | Howard |
| 2016/0023003 A1 | 1/2016 | Perryman |
| 2016/0038130 A1 | 2/2016 | Schaller |
| 2016/0067481 A1 | 3/2016 | Stone |
| 2016/0144163 A1 | 5/2016 | Floyd et al. |
| 2017/0007827 A1 | 1/2017 | Mehdizadeh |

IMPLANTABLE MEDICAL LEADS AND LEAD EXTENSIONS HAVING AN ENCAPSULATION BAND

RELATED APPLICATIONS

This application is a continuation of U.S. application Ser. No. 16/396,389, filed on Apr. 26, 2019.

TECHNICAL FIELD

Embodiments relate to implantable medical leads and/or lead extensions. More specifically, embodiments relate to implantable medical leads and/or lead extensions that include a band that encapsulates a portion of internal conductors.

BACKGROUND

Implantable medical systems include an implantable device that includes circuitry for providing stimulation therapy and/or physiological sensing. An implantable medical lead may be connected directly or indirectly via a lead extension to the implantable medical device to carry electrical signals between the location of interest within the body of the patient and the location of the implantable medical device. The implantable medical lead includes a lead body having electrodes near a distal end and these electrodes are positioned at the location of interest. A lead extension, when present between the implantable medical device and implantable medical lead, also has a lead body and has a distal end containing connectors within a lead bore that receives the proximal end of the lead. Electrical conductors are present within the lead body of the lead and/or lead extension and electrically connect the distal electrodes, or distal connectors of a lead extension, to contacts on a proximal end of the lead body. The proximal end of the lead and/or lead extension is coupled to the implantable medical device where the proximal contacts electrically couple to electrical connectors of the implantable medical device.

During implantation of the implantable medical system, once the lead has been implanted and an implantation stylet, if used, has been removed via the proximal end of the implantable medical lead, a clinician must insert the proximal end of the implantable medical lead into a lead bore of the implantable medical device or into a lead bore of a lead extension when present. Because the implantable medical lead engages various electrical connectors and seals within the implantable medical device or lead extension, an insertion force is necessary to insert the implantable medical lead. In some cases, this insertion force may cause the proximal end of the lead to buckle which makes insertion of the lead difficult and complicates the implantation procedure. Likewise, when a lead extension is present, a clinician must insert the proximal end of the implantable medical lead extension into a lead bore of the implantable medical device. Because the implantable medical lead extension engages various electrical connectors and seals within the implantable medical device, an insertion force is also necessary to insert the implantable medical lead extension. In some cases, this insertion force may cause the proximal end of the lead extension to buckle which makes insertion of the lead extension difficult and further complicates the implantation procedure.

SUMMARY

Embodiments address issues such as these and others by providing implantable medical apparatus, such as leads and/or lead extensions, that include a band of material on the proximal end that encapsulates a portion of the conductors within a lead body. Furthermore, the band may hold the conductors in a constrained and organized arrangement. Additionally, the band together with another body, such as a stiffener rod, stylet tube, and/or molding stylet, and lead body may provide a sealed arrangement that allows a proximal lumen of the lead body to be filled by injection molding material with the injection molding material being blocked from proceeding beyond the band.

A stiffener rod as mentioned above may be included in some embodiments while being absent from others. In those embodiments that include a stiffener rod, the stiffener rod increases the stiffness of the proximal end of the lead to reduce the likelihood of buckling during insertion. The stiffener rod may provide additional benefits such as strain relief. The stiffener rod may be coupled to the conductors within the lead by the band of material that encapsulates a portion of the conductors also being bonded to the stiffener rod.

Embodiments provide an implantable medical apparatus that includes a lead body having a proximal end and a distal end, the lead body defining a lumen. The implantable medical apparatus includes a proximal contact on the lead body in proximity to the proximal end and a distal element coupled to the lead body in proximity to the distal end. The implantable medical apparatus includes a conductor electrically coupled to the proximal contact and the distal element, and the conductor extends through the lumen. The implantable medical apparatus includes a stiffener rod present within the lumen and includes a non-conductive band present within the lumen and surrounding the stiffener rod. The non-conductive band encapsulates a portion of the conductor and being bonded to the stiffener rod.

Embodiments provide an implantable medical system that includes an implantable medical device and an implantable medical apparatus coupled to the implantable medical device. The implantable medical apparatus includes a lead body having a proximal end and a distal end, the lead body defining a lumen. The implantable lead includes a proximal contact on the lead body in proximity to the proximal end and a distal element coupled to the lead body in proximity to the distal end. The implantable medical lead includes a conductor electrically coupled to the proximal contact and the distal element, and the conductor extends through the lumen. The implantable medical lead includes a stiffener rod present within the lumen and includes a non-conductive band present within the lumen and surrounding the stiffener rod. The non-conductive band encapsulates a portion of the conductor and being bonded to the stiffener rod.

Embodiments provide a method of constructing an implantable medical apparatus. The method involves placing a stiffener rod near a proximal end of a conductor and placing a non-conductive band about the stiffener rod and a portion of the conductor. The method involves reflowing the non-conductive band to encapsulate the portion of the conductor and to bond to the stiffener rod. The method further involves surrounding the conductor, stiffener rod, and conductor with a lead body. The method also involves attaching a proximal contact in proximity to a proximal end of the lead body and electrically connecting the proximal contact to the conductor. Additionally, the method involves coupling a distal element to the distal end of the lead body and electrically connecting the distal element to the conductor.

Embodiments provide an implantable medical apparatus that is constructed by a method. The method involves placing a stiffener rod near a proximal end of a conductor and placing a non-conductive band about the stiffener rod and a portion of the conductor. The method involves reflowing the non-conductive band to encapsulate the portion of the conductor and to bond to the stiffener rod. The method further involves surrounding the conductor, stiffener rod, and conductor with a lead body. The method also involves attaching a proximal contact in proximity to a proximal end of the lead body and electrically connecting the proximal contact to the conductor. Additionally, the method involves coupling a distal element to the distal end of the lead body and electrically connecting the distal element to the conductor.

Embodiments provide a method of constructing an implantable medical apparatus. The method involves providing a lead body having a proximal end and a distal end, the lead body defining a lumen, a conductor electrically extending through the lumen, a stiffener rod present within the lumen, and a non-conductive band present within the lumen and surrounding the stiffener rod, the non-conductive band encapsulating a portion of the conductor and being bonded to the stiffener rod. The method further comprises injection molding an interior portion of the proximal end of the lead body.

DESCRIPTION OF THE DRAWINGS

FIG. 7AA shows an example of an implantable medical lead or lead extension with a band as well as a stylet tube where a lead body is not present.

FIG. 8AA shows a cross-sectional view made via an axial cut along the length of an example of an implantable medical lead or lead extension with a molding stylet and associated band as well as a stylet tube.

FIG. 8BB shows a cross-sectional view of the example of FIG. 8AA with the molding stylet removed.

DETAILED DESCRIPTION

Embodiments provide implantable medical apparatus, such as leads and/or lead extensions, of implantable medical systems that have a band of material that encapsulates a portion of internal conductors. The band may organize the conductors into a particular arrangement. Furthermore, the band may cooperate with an additional object, such as a stiffener rod or molding stylet, and lead body to provide a seal during injection molding of a proximal lumen of a lead body. A stiffened proximal end may also be provided by including a stiffener rod associated with the band. The stiffener rod adds stiffness while the associated band encapsulates a portion of the conductors adjacent to the stiffener rod while being bonded to the stiffener rod.

Figure 1:
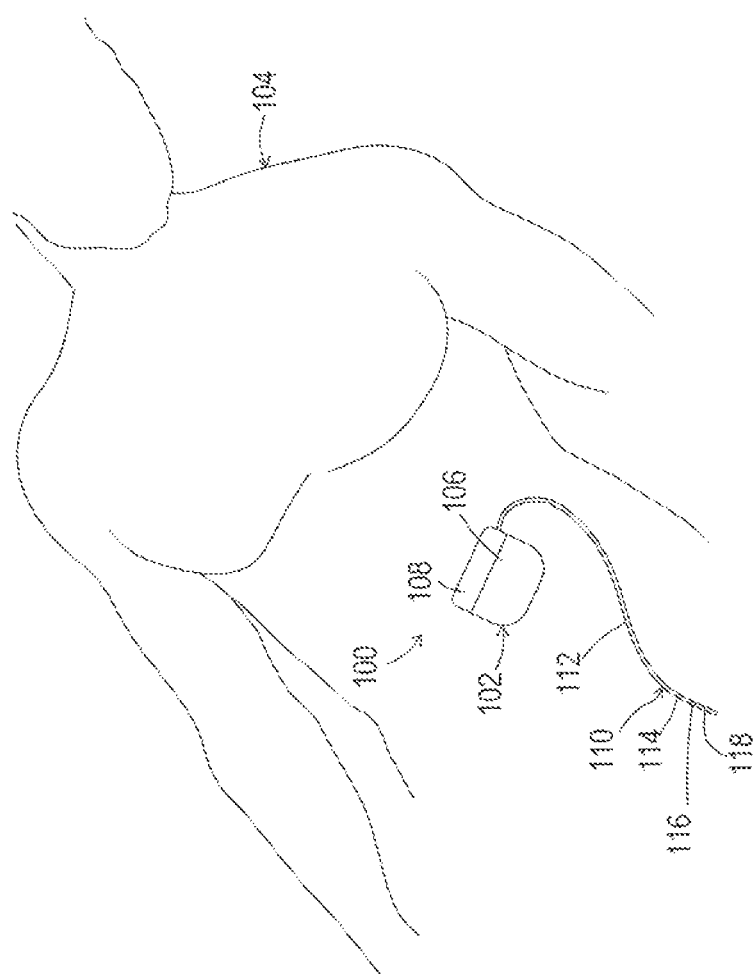
FIG. 1 shows a patient having an example of an implantable medical system that includes an embodiment of an implantable medical lead and/or lead extension with a proximal stiffener rod and associated band.

FIG. 1 shows an example of an operating environment for the various embodiments. An implantable medical system 100 is implanted within a body of a patient 104. The implantable medical system 100 includes an implantable medical device 102 coupled to an implantable medical lead 110 that may be used for stimulation and/or sensing. It will be appreciated that a lead extension 107, shown in FIG. 2B discussed below, may also be present and be connected between the lead 110 and the device 102. The implantable medical system 100 may be of various types, such as a neurostimulation system used for deep brain stimulation, spinal cord stimulation, peripheral nerve stimulation, a cardiovascular stimulation system, and the like. The implantable medical device 102 includes an outer casing 106 (e.g., the device "can" or "housing") as well as a header 108 that includes a bore where a proximal end of the stimulation lead 110 is positioned. The lead 110 includes a lead body 112 and a set of distal elements, namely electrodes 114, 116, 118 on a distal end of the lead body 112 which is positioned at a stimulation site within the body of the patient 104. While three distal electrodes are shown in this example and in FIG. 2A, any number of electrodes may be present. For example, the embodiment shown in FIGS. 3 and 4 and discussed below include eight conductors that interconnect eight proximal contacts to eight distal electrodes. A lead extension has distal elements that are distal connectors, rather than distal electrodes, coupled to the distal end of the lead body of the lead extension.

Signals are delivered through conductors of the stimulation lead 110, and lead extension when present, with at least one of the electrodes where stimulation signals enter the tissue of the patient 104 and/or physiological signals are sensed from the tissue. Stimulation may be bipolar (between multiple ones of the electrodes of stimulation lead 110 or multiple such leads). In some embodiments, bipolar stimulation may be delivered between electrodes on different leads. Alternatively, stimulation may be unipolar. The outer casing 106 may be conductive and serve as an electrode where unipolar stimulation is being provided such that stimulation is delivered between an electrode on a lead and the casing 106. Stimulation could also be multipolar such that it is delivered between multiple electrodes on one or more stimulation leads as well as between at least one of the multiple electrodes and casing 106.

The foregoing example provides an example of a lead 110 that may provide both the stimulation signal and sensing function for the physiological signal. In still another example, the one lead may be used to provide the stimulation while another lead may be used to provide the sensing function. In yet another example, stimulation may be provided between electrodes residing on multiple different leads (e.g., between electrode 1 on lead 1 and electrode 2 on lead 2), and sensing may be performed between multiple electrodes residing on multiple different leads. The set of multiple leads providing the stimulation electrodes may, but need not, be the same set of multiple leads providing the sensing electrodes. Where multiple leads, and multiple lead extensions when necessary, are present in an implantable medical system, one or more of the multiple leads and/or lead extensions may include a band of material encapsulating a portion of internal conductors as discussed in more detail below.

The one or more leads used for providing the stimulation signals and/or for sensing the physiological signals may be of various types. In one example, a lead having a simple electrode array geometry may be used for stimulation and/or for sensing. An example of a simple electrode array geometry may include one or more ring electrodes distributed at different axial positions along the length of the lead 110. Another example of a simple electrode array geometry is a planar array of electrodes on a paddle lead. In another embodiment, one or more leads used for providing the stimulation signal and/or for sensing the physiological signals may have a complex electrode array geometry such as electrodes at multiple non-planar or non-coaxial positions or at different angular positions about the periphery, e.g., circumference, of the lead.

When unipolar stimulation is being provided, the stimulation signals may be delivered using various unipolar arrangements. A unipolar stimulation arrangement generally refers to the use of an anode on the conductive outer casing 106 that sources current and one or more cathodes on one or more leads (e.g., 110) that sink current. However, embodiments may utilize an anode that is instead in a proximal position on the lead 110 which approximates the use of the outer casing 106 as the anode.

Figure 2A:
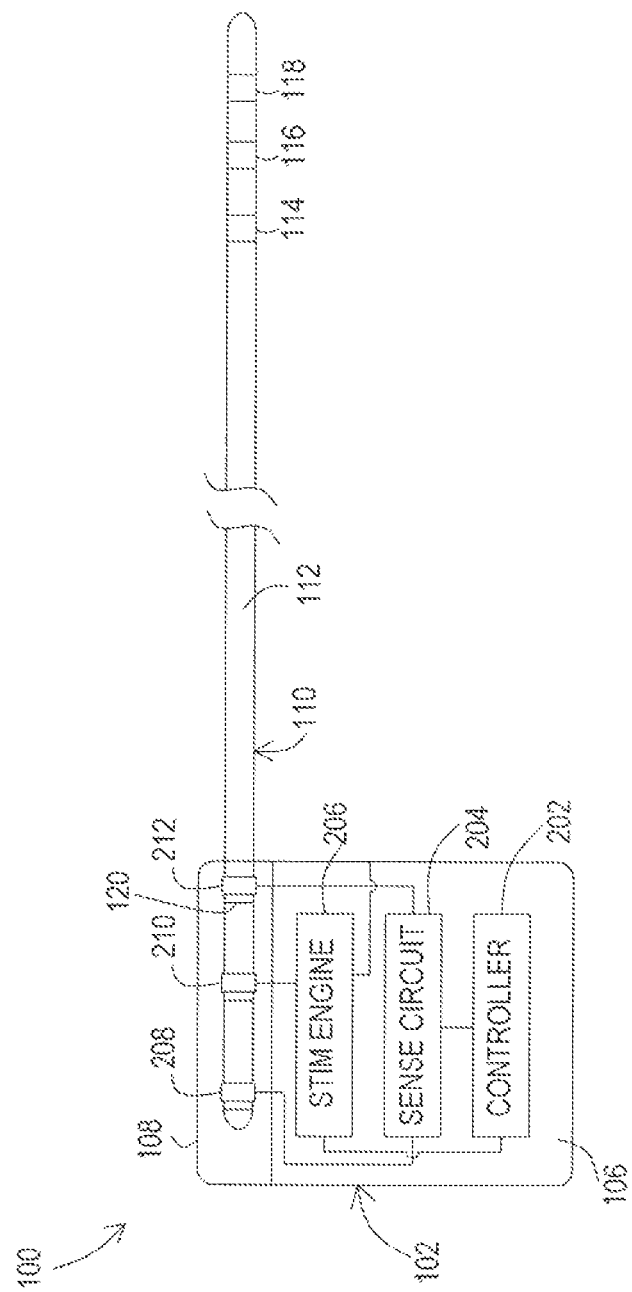
FIG. 2A shows an example of an implantable medical system including a medical device attached to an implantable medical lead or lead extension with a proximal stiffener rod and associated band.

FIG. 2A shows the example of the implantable medical system 100 in more detail. Here, the stimulation device 102 includes a stimulation engine 206, a sensing circuit 204, or both. The stimulation device 102 also includes a controller 202. The stimulation engine 206 produces the stimulation pulses and recharge pulses applied to the stimulation pathway via electrical connections such as connection 210 to the lead 110 within the header block 108. The sensing circuit 204 may be present to capture physiological signals via connections, such as connections 208, 212 to the lead 110 within the header block 108.

In this example, the controller 202 controls the operation of the sensing circuit 204 and the stimulation engine 206. The controller 202 may be of various forms. For instance, the controller 202 may comprise a general purpose programmable processor that implements programming instructions to bring about the operation of the stimulation engine 206 and/or the sensing circuit 204. As other examples, the controller 202 may comprise a dedicated purpose processor and/or hardwired digital logic.

The implantable medical lead 110 includes proximal contacts 120. These proximal contacts 120 electrically couple to corresponding electrical connectors such as 208, 210, and 212 of the implantable medical device when the proximal end of the implantable medical lead 110 is inserted into the lead bore of the implantable medical device 102. Via conductors within the lead body 112, signals may be exchanged between the circuitry of the implantable medical device 102 and the distal electrodes 114, 116, and 118.

Figure 2B:
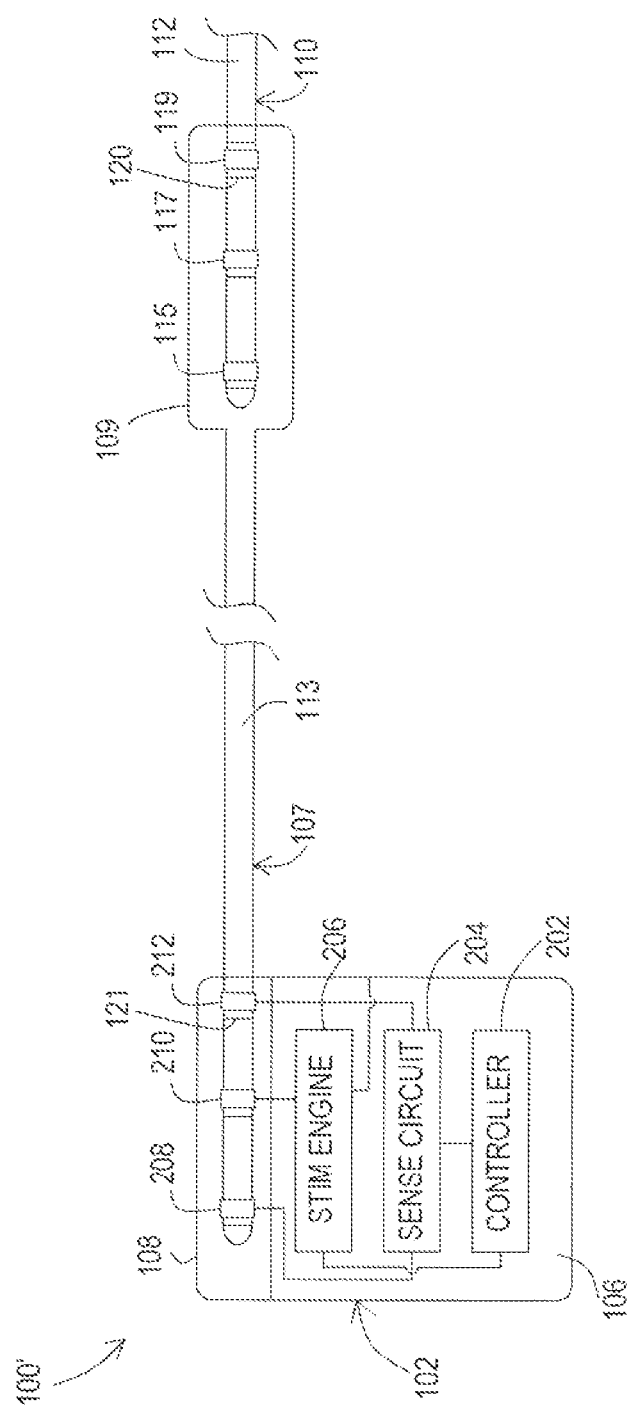
FIG. 2B shows an example of an implantable medical system including a medical device attached to an implantable medical lead extension with a proximal stiffener rod and associated band, and with an implantable medical lead attached to the lead extension.

FIG. 2B shows another example of the implantable medical system 100' where the stimulation device 102 includes the stimulation engine 206, the sensing circuit 204, or both. The stimulation device 102 also includes the controller 202. The stimulation engine 206 produces the stimulation pulses and recharge pulses applied to the stimulation pathway via the electrical connections such as connection 210 to a lead extension 107 within the header block 108. The sensing circuit 204 may be present to capture physiological signals via connections, such as connectors 208, 212 to the lead extension 107 within the header block 108.

The implantable medical lead extension 107 includes proximal contacts 121. These proximal contacts 121 electrically couple to the corresponding electrical connectors such as 208, 210, and 212 of the implantable medical device 102 when the proximal end of the implantable medical lead extension 107 is inserted into the lead bore of the implantable medical device 102. Via conductors within the lead body 113, signals may be exchanged between the circuitry of the implantable medical device 102 and the distal connectors 115, 117, and 119 coupled to and present within a distal connector housing 109 forming a distal end of the lead body 113.

The lead 110 has the proximal end present and in a fixed position within a lead bore of the distal connector housing 109. The proximal contacts 120 of the lead 110 electrically couple to the corresponding electrical connectors 115, 117, and 119 of the lead extension. Via the conductors within the lead body 113, signals may be exchanged between the circuitry of the implantable medical device 102 and the distal connectors 115, 117, and 119 coupled to and present within a distal connector housing 109 forming a distal end of the lead body 113.

Figure 3:
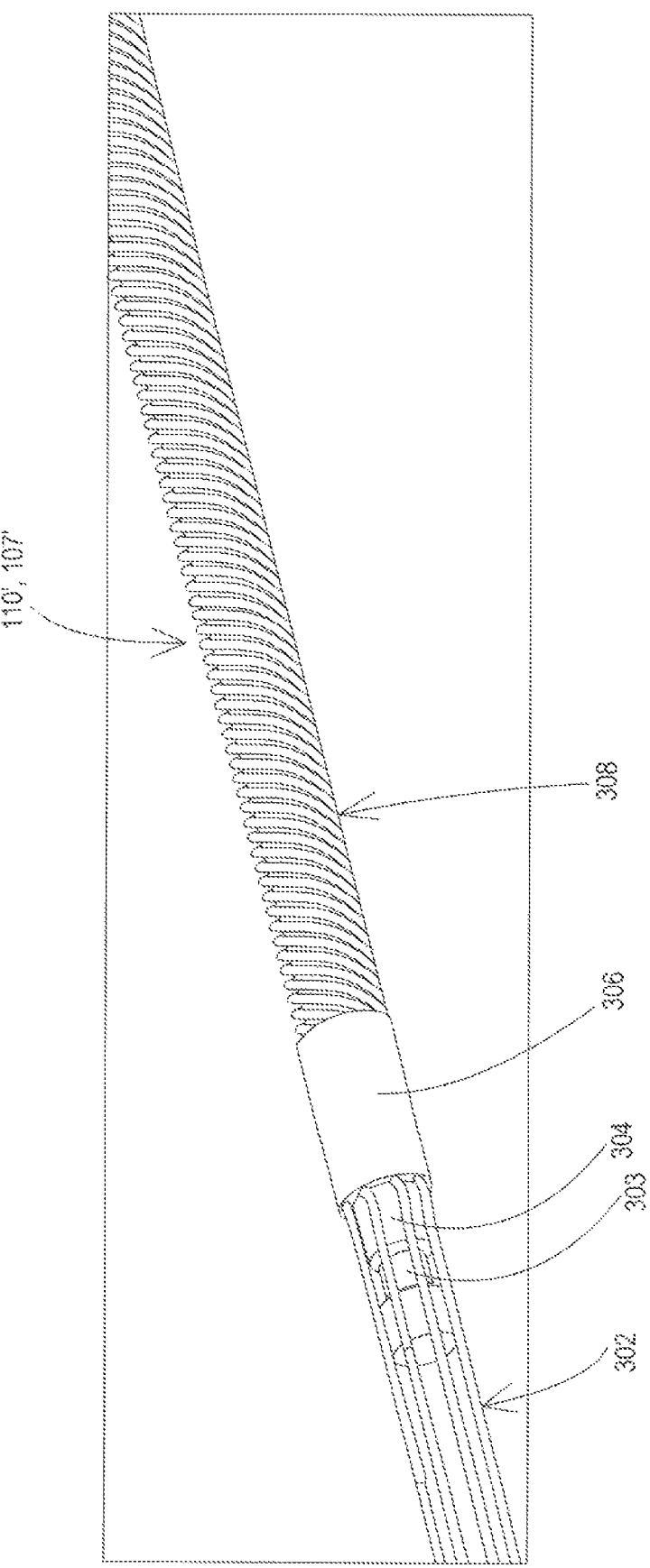
FIG. 3 shows an example of an implantable medical lead or lead extension with a proximal stiffener rod and associated band where a lead body is not present.
Figure 4:
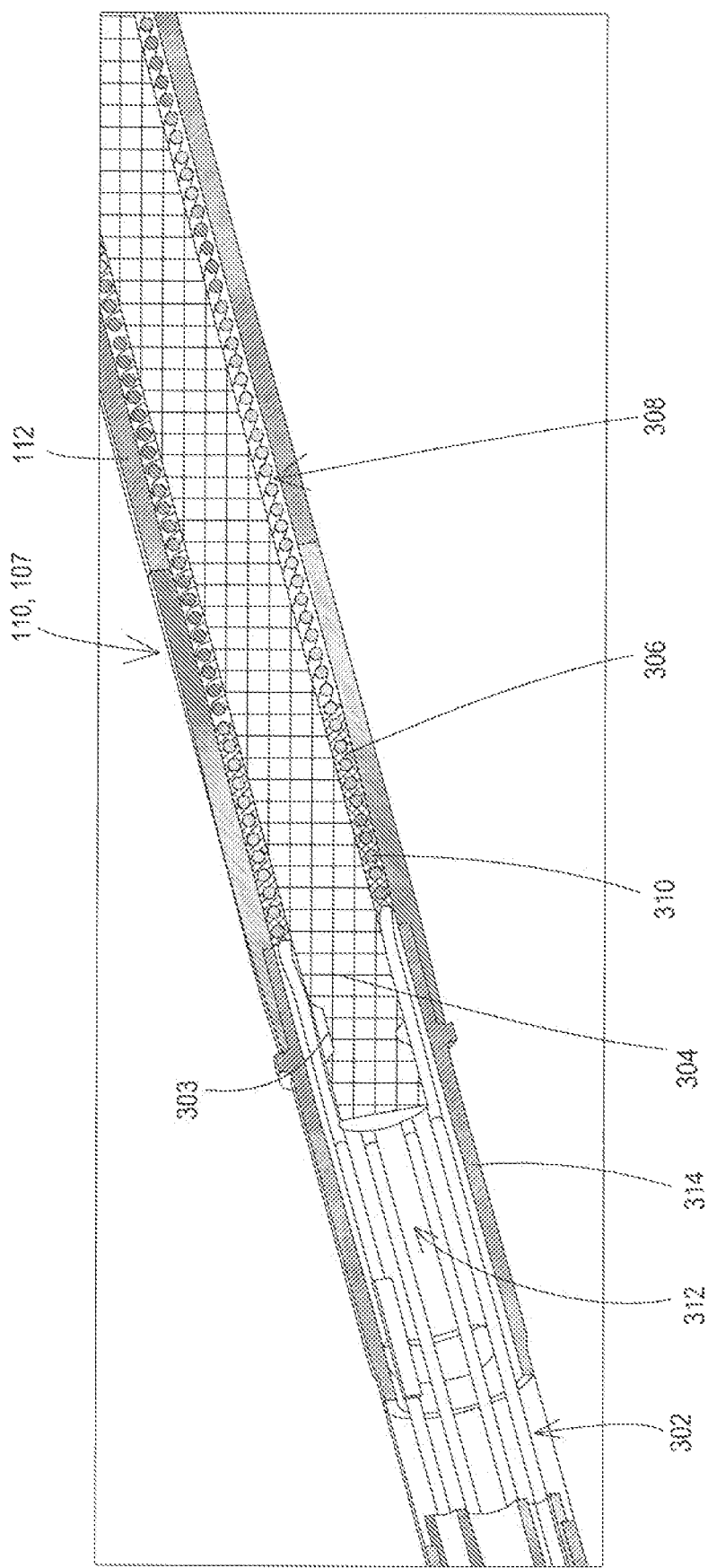
FIG. 4 shows a cross-sectional view made via an axial cut along the length of an example of an implantable medical lead or lead extension with a proximal stiffener rod and associated band.

FIG. 3 shows a proximal area of the lead 110' or lead extension 107' modified for purposes of illustration to be without the lead body 112 in order to reveal the internal configuration of components. FIG. 4 shows a cross-sectional view of the lead 110 or lead extension 107 to further illustrate the configuration. The proximal area includes a proximal end 302 of the filar conductors present within a lumen 312 of the lead body 112. In this example, the proximal end 302 of the conductors is linear, as the conductor are directed to the respective proximal contacts 120 of FIG. 2A or 2B. In this example, the conductors extend in the distal direction to a band 306 where the conductors include a portion 310 that is encapsulated within the band 306 and that also begins to coil. The conductors of this example continue distally in a coiled configuration through the band 306 and then continue as a coil 308 distally of the band toward the electrodes. While this example shows the conductors forming a coil, it will be appreciated that in other examples the conductors may remain linear over their full length and/or remain linear in the area of the band 306.

The band 306 which is also present within the lumen 312 is constructed of a non-conductive material that has been reflowed from an initial state that surrounds the conductors to the state shown that encapsulates the portion 310 of the coiled conductors 308. Reflowing the band 306 is done by heating the band 306 while applying pressure until the material of the band 306 is able to flow between the coil filar conductors. The reflowed non-conductive band 306 also contacts and becomes bonded to a stiffener rod 304, discussed in more detail below, when being reflowed. Examples of such a material for the band 306 include but are not limited to various reflowed polymers such as polyurethane or other thermoplastic that re-melt when heated. In one particular example, the band 306 is constructed of reflowed polyurethane having a durometer Shore hardness rating of 80A.

The band 306 may serve several purposes. By encapsulating the portion 310 of the coiled conductors 308, the band 306 holds the conductors in a constrained and organized fashion at the transition from the linear portion 302 to the coiled arrangement 308. During construction of the lead and/or lead extension, creating this constrained and organized arrangement of the coiled conductors is beneficial for downstream lead and/or lead extension manufacturing processes. For examples where the conductors remain linear over their full length and/or in the area where the band 306 is present, the band 306 may properly space and organize linear conductor portions that are encapsulated by the band 306.

For embodiments of the lead and/or lead extension that include a stiffener rod, the band 306 also aids in holding the stiffener rod 304 in a fixed position relative to the band 306 and coil 308 in the proximal area of the lead 110 and/or lead extension 107 by being bonded to the stiffener rod 304 when the band 306 is reflowed. The band 306 also serves as a seal together with the stiffener rod 304 during injection molding of the interior or lumen 312 of the proximal area of the lead 110 and/or lead extension 107. This injection molding process is discussed in more detail below with reference to FIGS. 5 and 6. As further described below, the reflowed band 306 may contact the interior surface of the lead body 112 but during the injection molding process, the band 306 may also be pinched against the lead body 112 to further form the seal.

The band 306 may be of various lengths in order to provide these benefits. For instance, in one example of a neurostimulation lead or lead extension, the length of the band 306 may range from 0.05 inch to 0.09 inch in order to be pinched against the lead body 112 and provide the seal during the injection molding. It will be appreciated that many different lengths are appropriate in order to pinch the band 306 and to encapsulate the portion of the lead or lead extension conductors.

The stiffener rod 304 of this example resides within the interior of the coiled conductor 308 and thus also resides in the lumen 312 of the proximal area of the lead 110 and/or lead extension 107. The stiffener rod 304 may likewise be surrounded by linear conductors in examples where the conductors remain linear over their full length and/or in the region where the stiffener rod 304 is present. The stiffener rod 304 of this example further extends distally through the area that is just distal of the electrical contacts 120. The stiffener rod 304 thereby adds stiffness to the proximal area where a clinician will grasp the lead body 112 when attempting to insert the proximal end of the lead 110 or lead extension 107 into the lead bore of the implantable medical device 102, or when attempting to insert the proximal end of the lead 110 into a distal end lead bore of a lead extension. The stiffener rod 304 causes the proximal end of the lead 110 and/or lead extension 107 to resist buckling during the insertion procedure that might otherwise occur due to the insertion force needed to overcome friction within the lead bore.

The stiffener rod 304 may also provide additional benefits. For instance, the stiffener rod 304 may provide strain relief for acute bending of the lead 110 and/or lead extension 107 near the proximal end.

The stiffener rod 304 may be constructed of materials such as but not limited to polyurethane, polyether ether ketone (PEEK), polysulfone, and the like. In one particular example, the band 306 is constructed of polyurethane having a durometer Shore hardness rating of 75 D which provides a relatively high degree of stiffness.

The size of the stiffener rod 304 may vary. However, the diameter of the stiffener is provided as the desired inside diameter of the coil or slightly smaller so that the stiffener rod 304 properly fits in the interior of the coil 308. The stiffener rod 304 may also be of various lengths in order to provide the stiffening benefit. For instance, in one example of a neurostimulation lead or lead extension, the length of the stiffener rod 304 may range from three inches to four inches. The length of the stiffener rod 304 may be sized to the requirements for a physician gripping the lead but may also be sized to provide any desired degree of strain relief.

Additionally, the stiffener rod 304 may include the reduced diameter section or groove 303 on the proximal end. When the proximal end of the lead 110 or lead extension 107 is injection molded, the injection molding material may fill the groove 303. The injection molding material being present in the groove 303 further holds the stiffener rod 304 in a fixed position within the lead body 112.

Figure 5:
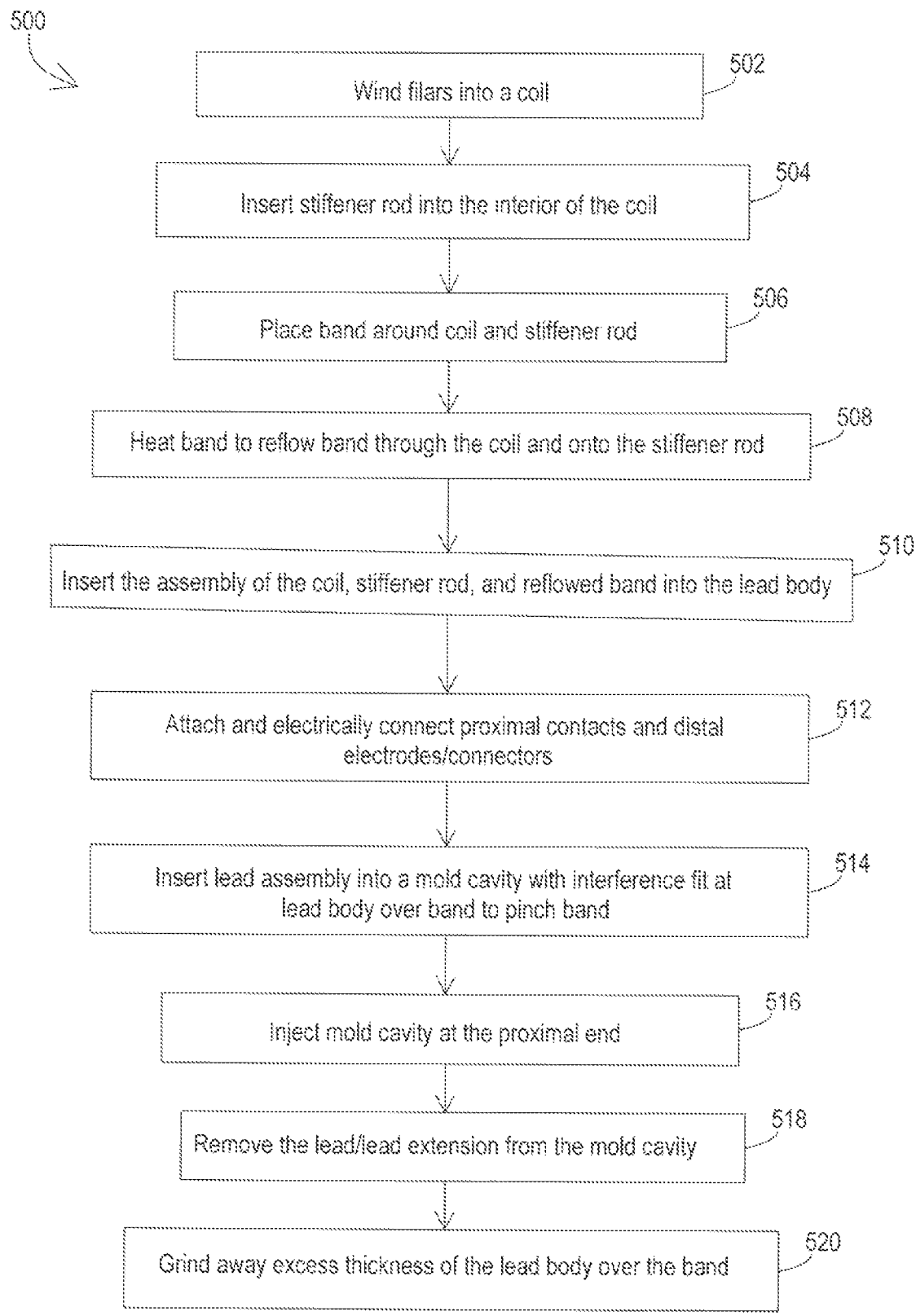
FIG. 5 shows manufacturing steps that may be taken to manufacture an example of an implantable medical lead or lead extension that includes a stiffener rod and associated band.

FIG. 5 shows an example of a process for creating the implantable medical lead and/or lead extension having the stiffener rod 304 and associated band 306. For the lead 110 or lead extension 107 example shown in FIGS. 3 and 4 where the conductors become coiled at the band 306, the process begins by the filar conductors being wound into a coil at an operation 502. A proximal portion 302 of the filar conductors may remain linear as discussed above. Furthermore, for examples where the conductors are not coiled, then the operation 502 is omitted.

Once the filar conductors are in the desired configuration, such as coiled via operation 502, the stiffener rod 304 is inserted into the interior of the proximal end of the coil at an operation 504. For examples where the filar conductors are linear in the area where the stiffener rod 304 is to be positioned, the proximal areas of the filars are positioned in linear fashion about the stiffener rod 304. In either case, the stiffener rod 304 is surrounded by the filar conductors.

At this point the band 306 that has not yet been reflowed is placed around the filar conductors and stiffener rod 304 at an operation 506. The band 306 is positioned at the desired axial location of the stiffener rod 304 and conductors. In the example of FIGS. 3 and 4, the band 306 is placed such that a proximal end of the band is positioned on the filar conductors at the point where the filar conductors begin to coil such that the portion 310 of the conductors that are being encapsulated are fully coiled within the band 306. Additionally, in the example of FIGS. 3 and 4, the stiffener rod 304 has a proximal portion extending proximally of the proximal end of the band 306.

Once the band 306 is positioned as desired, the band 306 is heated to reflow the band onto the portion 310 of the filar conductors and stiffener rod 304 at an operation 508. This reflow or melting of the band 306 causes the band 306 to encapsulate the portion 310 of the filar conductors and also contact and bond to the stiffener rod 304. This locks the stiffener rod 304 to the encapsulated portion 310 of the filar conductors.

The assembly of the filar conductors, band 306, and stiffener rod 304 may then be inserted into the empty tubular lumen 312 of the lead body 112 at an operation 510. The lumen 312 of the lead body 112 is large enough to receive the coiled conductors 308 without restriction. The lumen 312 of the lead body 112 is also large enough to receive the reflowed band 306, although the reflowed band 306 may have an interference fit within the lumen 312. Once inserted, the filar conductors extend distally so that the distal end is in position to connect to where distal electrodes of the lead, or distal connectors of the lead extension, will be while the proximal end of the filar conductors is in position to connect to where the proximal contacts will be.

The proximal contacts and distal electrodes, or distal connectors of a distal lead bore for a lead extension, may be attached to the lead body, if not already present thereon, and then electrically connected to the filar conductors at an operation 512. This electrical connection may be done in the typical manner for implantable medical leads and/or lead extensions where the filar conductor is directed through an aperture in the lead body to the corresponding proximal contact or distal electrode or distal connector, and then a weld or other electrically conductive bond is formed.

Figure 6:
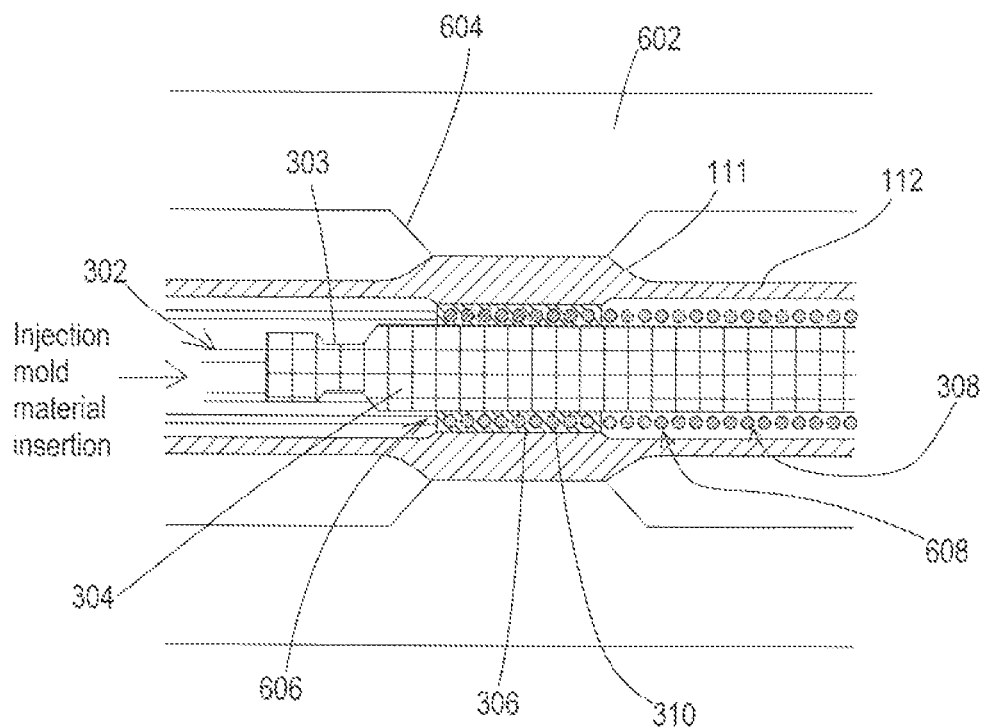
FIG. 6 shows a cross-sectional view of a mold cavity and implantable medical lead or lead extension that includes a stiffener rod and is positioned within the mold cavity when injection molding a proximal end lumen of the implantable medical lead or lead extension.

At this point, the proximal lumen 312 of the lead body 112 that contains the linear proximal ends 302 of the filar conductors remains open. Therefore, in this example, the proximal end is completed by filling the proximal lumen 312 with injection molding material. To accomplish this, the proximal end of the lead 110 and/or lead extension 107 is inserted into a mold cavity at an operation 514. An example of the mold cavity 602 is shown in FIG. 6 where the lead 110 or lead extension 107 has been inserted for purposes of injection molding of the proximal end of the lumen 312.

In this example, the mold cavity 602 is provided with an annular protrusion 604. The lead body 112 of this example also has an annular protrusion 111 where the lead body is thicker and thus has a larger diameter than the remainder of the lead body 112. The protrusion 604 is brought into contact with the protrusion 111 via an interference fit due to the protrusion 111 having a contact surface with a diameter greater than the diameter of the contact surface of the protrusion 604. Thus, the protrusion 604 creates radially inward pressure at the protrusion 111. This radially inward pressure causes the lead body 112 to pinch tightly against the reflowed band 306, which creates a seal 606. It will be appreciated that an annular protrusion 604 of the mold cavity 602 may be sized to apply radially inward pressure onto the lead body 112 in the area of the band 306 without the lead body 112 including the annular protrusion 111. However, the annular protrusion 604 may create a degree of damage to the outer surface of the lead body where the radially inward pressure is applied, so including the annular protrusion 111 on the lead body 112 allows the damaged area to be removed by removal of the annular protrusion 111 as further discussed below.

The proximal lumen 312 of the lead and/or lead extension is then filled with injection material, such as polyurethane, at an operation 516. This closes the lumen 312 to isolate the conductors and the connections to the proximal contacts while adding stiffness in the proximal area where the contacts are located. Because the band 306 creates a seal together with the lead body 112 and stiffener rod 304, the injection molding material is blocked from proceeding past the band 306. Therefore, the coiled conductors 308 distal of the band 306 are not encapsulated or otherwise constrained by the injection molded material, and the lead 110 and/or lead extension 107 retains flexibility distally of the stiffener rod 304 while avoiding flex fatigue issues.

Once the injection molding is complete, the lead 110 and/or lead extension 107 is removed from the mold cavity at an operation 518. However, the protrusion 111 of this example remains on the lead body 112. Therefore, in this example, the excess thickness of the lead body 112 forming the protrusion 111 is ground away at an operation 520. The grinding of this example results in the lead body 112 having a same diameter at the area where the band 306 is located and adjacent areas. It will be appreciated that the grinding may result in a different diameter than the adjacent areas. As discussed above, the annular protrusion 111 may be damaged on the surface due to the mold protrusion 604 and grinding away the annular protrusion 111 thereby removes the damaged area, exposing the undamaged lead body beneath the protrusion 111. It will also be appreciated that the area of the lead body 112 damaged by the mold protrusion 604 may be left as is, such as for examples where there is no annular protrusion 111 during the injection molding process.

The resulting lead 110 and/or lead extension 107 is thereby provided with an increased proximal end stiffness via the stiffener rod 304 which allows the clinician to insert the lead 110 and/or lead extension 107 with a reduced likelihood of buckling. Additionally, the stiffener rod 304 is held in place via the bond to the band 306 which encapsulates the conductors and may also be held in place via the injection molding material filling the groove 303 discussed above.

While embodiments disclosed above describe a stiffener rod that is bonded to the band, other embodiments of the implantable medical lead and/or lead extension may omit the stiffener rod, such as where a stylet lumen is to be created from the proximal end through the band and to the distal end. FIGS. 7A-10B and the related discussion below provide embodiments where the stylet lumen is present.

Figure 7A:
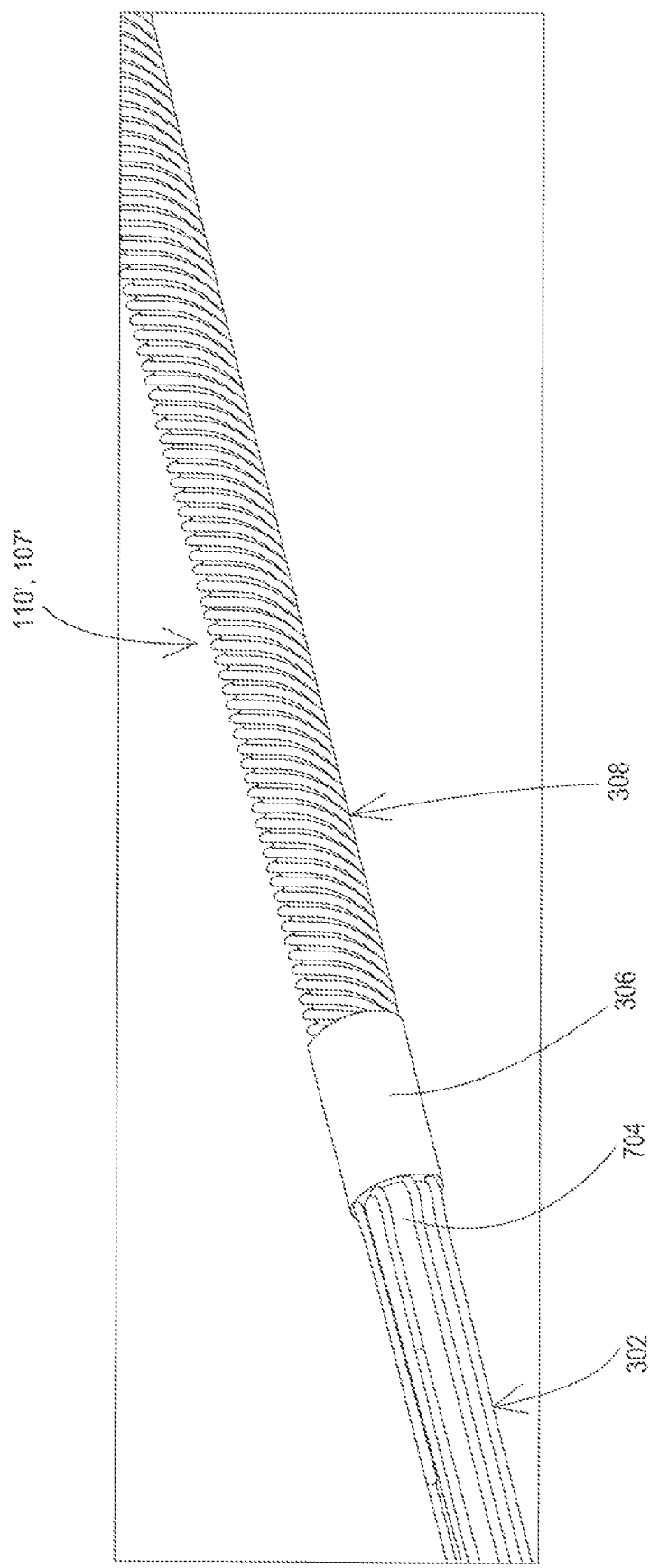
FIG. 7A shows an example of an implantable medical lead or lead extension with a molding stylet and associated band where a lead body is not present.
Figure 7A:
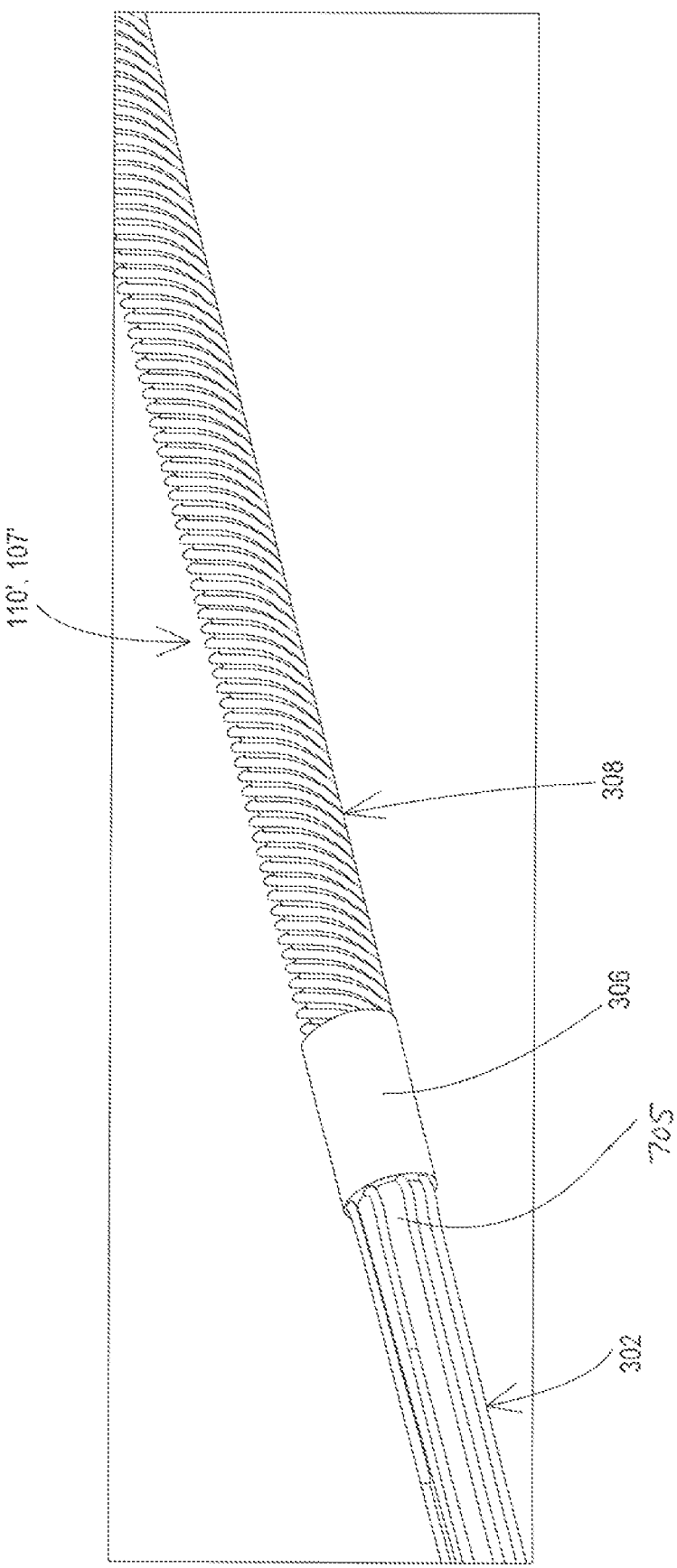
Figure 7B:
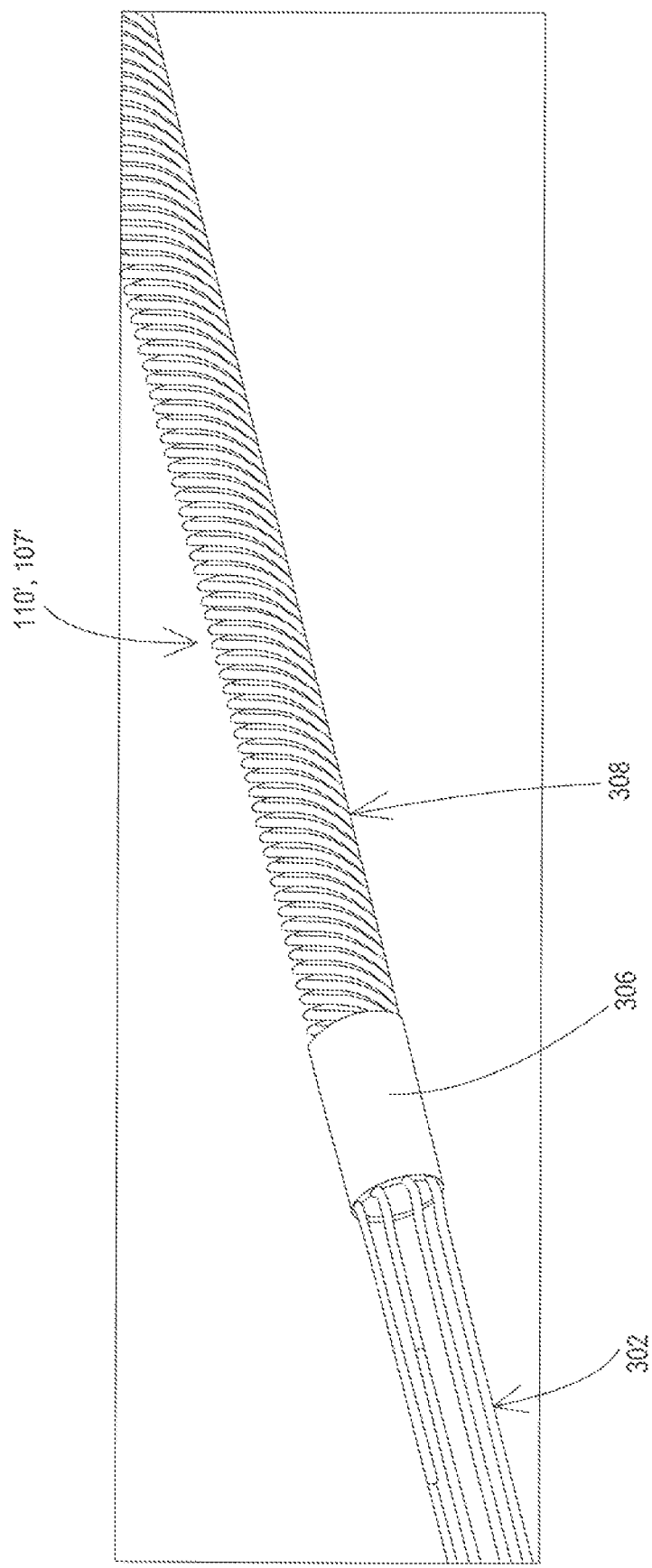
FIG. 7B shows the example of FIG. 7B with the molding stylet removed.
Figure 8A:
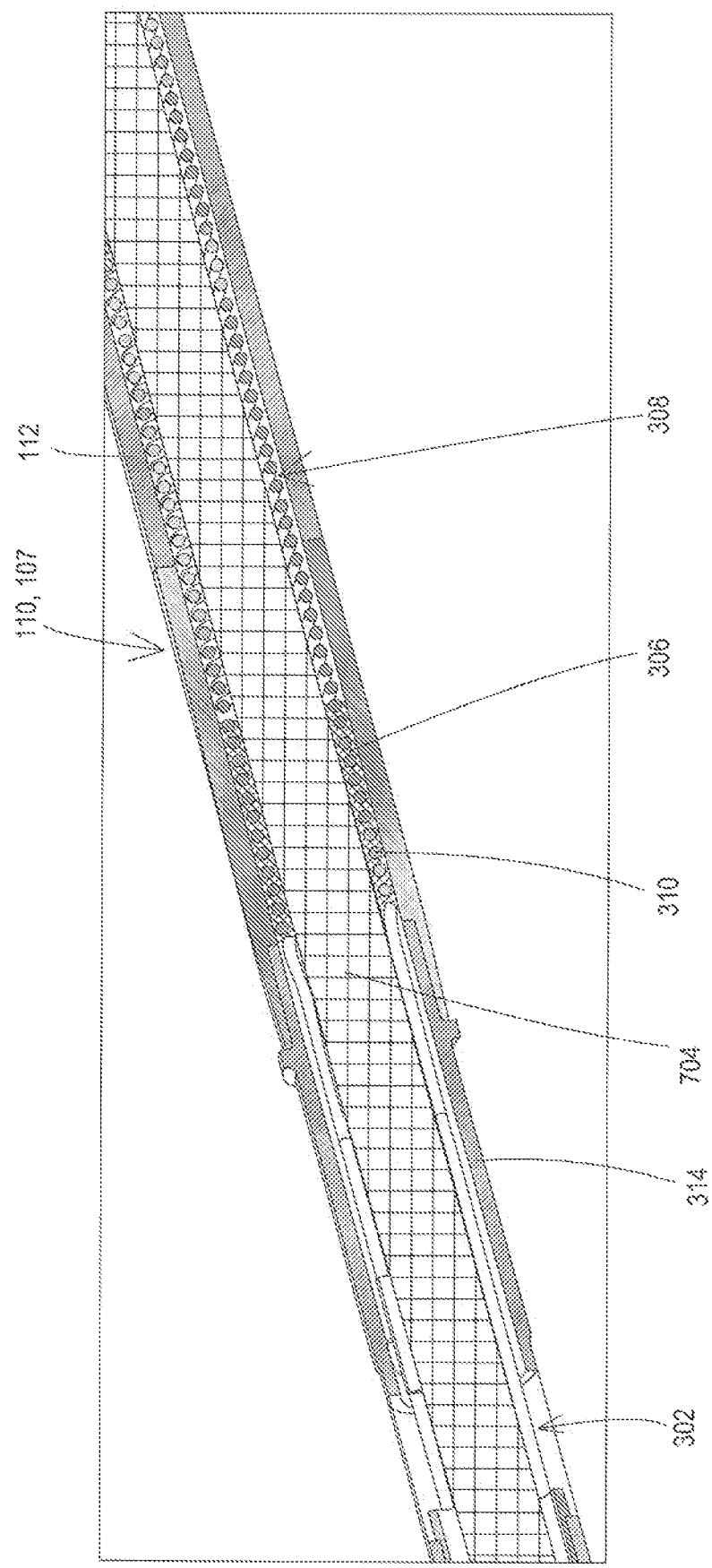
FIG. 8A shows a cross-sectional view made via an axial cut along the length of an example of an implantable medical lead or lead extension with a molding stylet and associated band.
Figure 8A:
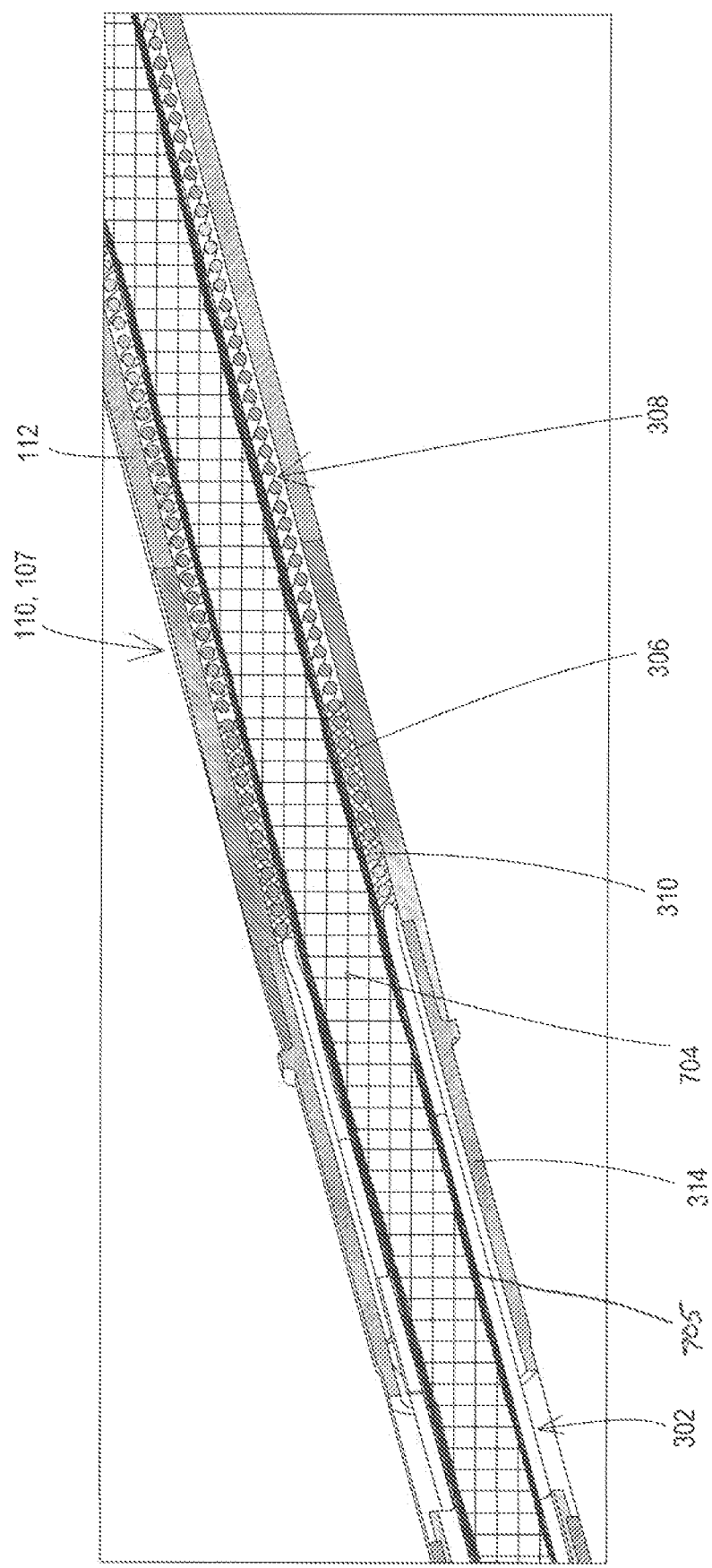
Figure 8B:
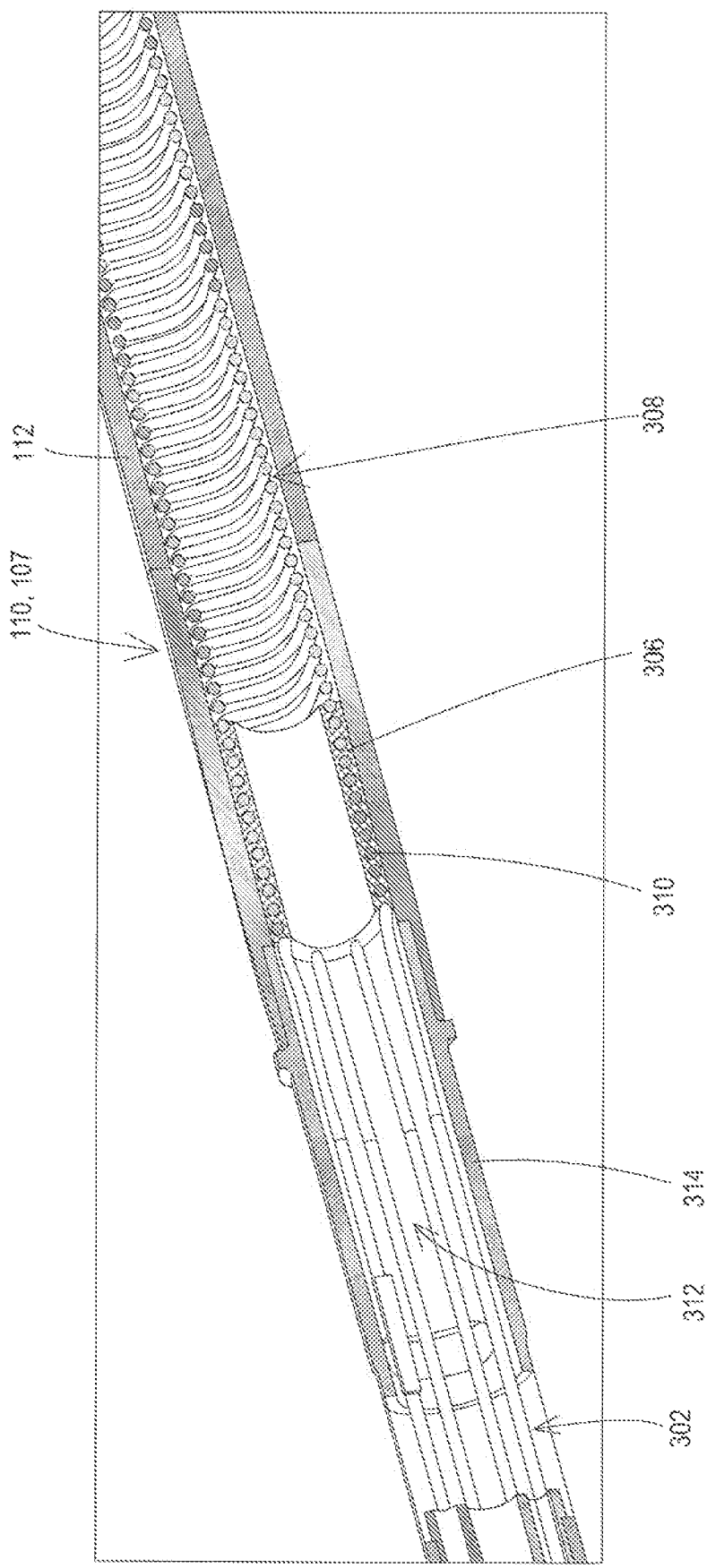
FIG. 8B shows a cross-sectional view of the example of FIG. 8A with the molding stylet removed.
Figure 8B:
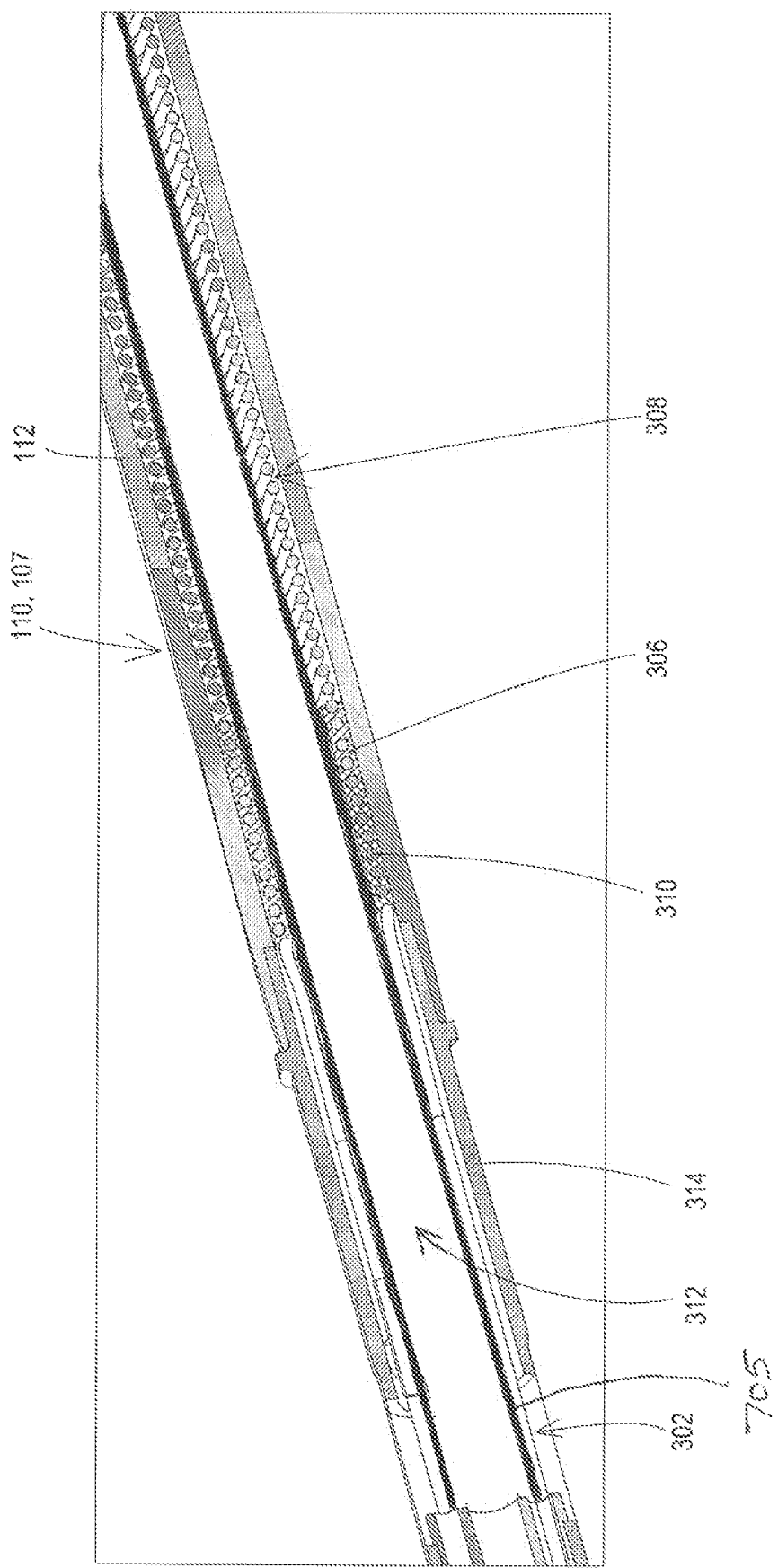

FIGS. 7A and 7B show a proximal area of the lead 110' or lead extension 107' that is modified for purposes of illustration to be without the lead body 112 in order to reveal the internal configuration of components. FIG. 7A shows the presence of a molding stylet 704 within the stylet lumen 312 provided by the lead body 112 and conductors. FIG. 7B shows the absence of the molding stylet 704 to reveal the stylet lumen 312 that is present through the band. FIGS. 8A and 8B show a cross-sectional view of the lead 110 or lead extension 107 to further illustrate the configuration. The proximal area in this embodiment also includes a proximal end 302 of the filar conductors present within the stylet lumen 312 of the lead body 112. In this example, the proximal end 302 of the conductors is linear, as the conductor are directed to the respective proximal contacts 120 of FIG. 2A or 2B. In this example, the conductors extend in the distal direction to the band 306 where the conductors include the portion 310 that is encapsulated within the band 306 and that also begins to coil. The conductors of this example continue distally in a coiled configuration through the band 306 and then continue as a coil 308 distally of the band toward the distal electrodes or distal connectors. While this example shows the conductors forming a coil, it will be appreciated that in other examples the conductors may remain linear over their full length and/or remain linear in the are the area of the band 306.

The band 306 which is also present within the lumen 312 while providing a continuation of the lumen 312 once the molding stylet 704 is removed is constructed of a non-conductive material that has been reflowed from an initial state that surrounds the conductors to the state shown that encapsulates the portion 310 of the coiled conductors 308. Examples of such a material for the band 306 include but are not limited to various reflowed polymers such as polyurethane or other thermoplastic that re-melt when heated. In one particular example, the band 306 is constructed of reflowed polyurethane having a durometer Shore hardness rating of 80A.

The band 306 may still serve several purposes despite the absence of a stiffener rod. By encapsulating the portion 310 of the coiled conductors 308, the band 306 holds the conductors in a constrained and organized fashion at the transition from the linear portion 302 to the coiled arrangement 308. As previously discussed, during construction of the lead and/or lead extension, creating this constrained and organized arrangement of the coiled conductors is beneficial for downstream lead and/or lead extension manufacturing processes. For examples where the conductors remain linear over their full length and/or in the area where the band 306 is present, the band 306 may properly space and organize linear conductor portions that are encapsulated by the band 306.

The band 306 also serves as a seal together with the molding stylet 704 during injection molding about an outer circumference of the interior of lumen 312 of the proximal area of the lead 110 and/or lead extension 107. This injection molding process is discussed in more detail below with reference to FIGS. 9 and 10. As further described below, the reflowed band 306 may contact the interior surface of the lead body 112 but during the injection molding process, the band 306 may also be pinched against the lead body 112 to further form the seal.

As with the prior embodiments, the band 306 of these embodiments that omit the stiffener rod may also be of various lengths in order to provide these benefits. For instance, in one example of a neurostimulation lead or lead extension, the length of the band 306 may range from 0.05 inch to 0.09 inch in order to be pinched against the lead body 112 and provide the seal during the injection molding. It will be appreciated that many different lengths are appropriate in order to pinch the band 306 and to encapsulate the portion of the lead or lead extension conductors.

The molding stylet 704 of this example resides within the interior of the coiled conductor 308 and thus also resides in the lumen 312 of the proximal area of the lead 110 and/or lead extension 107 only during construction of the lead or lead extension. A handle of the molding stylet 704 may remain external of the lead body 112 and therefore be easily grasped for removal from the stylet lumen 312 once assembly is complete. The molding stylet 704 of this example further extends distally through the area at least to the interior of the band 306.

The molding stylet 704 may be constructed of rigid materials such as but not limited to metals like stainless steel or titanium or other rigid materials like polyurethane, polyether ether ketone (PEEK), polysulfone, and the like. However, the surface of the molding stylet 704 should be such that when the band 306 is reflowed, the band 306 does not bond to the molding stylet 704 but merely abuts it in a manner that allows the molding stylet 704 to be removed from the lumen within the band 306. For instance, a coating may be applied to the molding stylet 704 to eliminate such bonding while reducing resistance to the movement of the molding stylet 704.

The diameter of the molding stylet 704 is chosen based on the desired size of the lumen through the band 306. This lumen size must be adequate to allow an implantation stylet to pass through the lumen of the ban 306, as the diameter of the molding stylet 704 establishes the diameter of the lumen through the band 306 when the reflowed material of the band 306 flows until reaching and hardening against the surface of the molding stylet 704.

Figure 9:
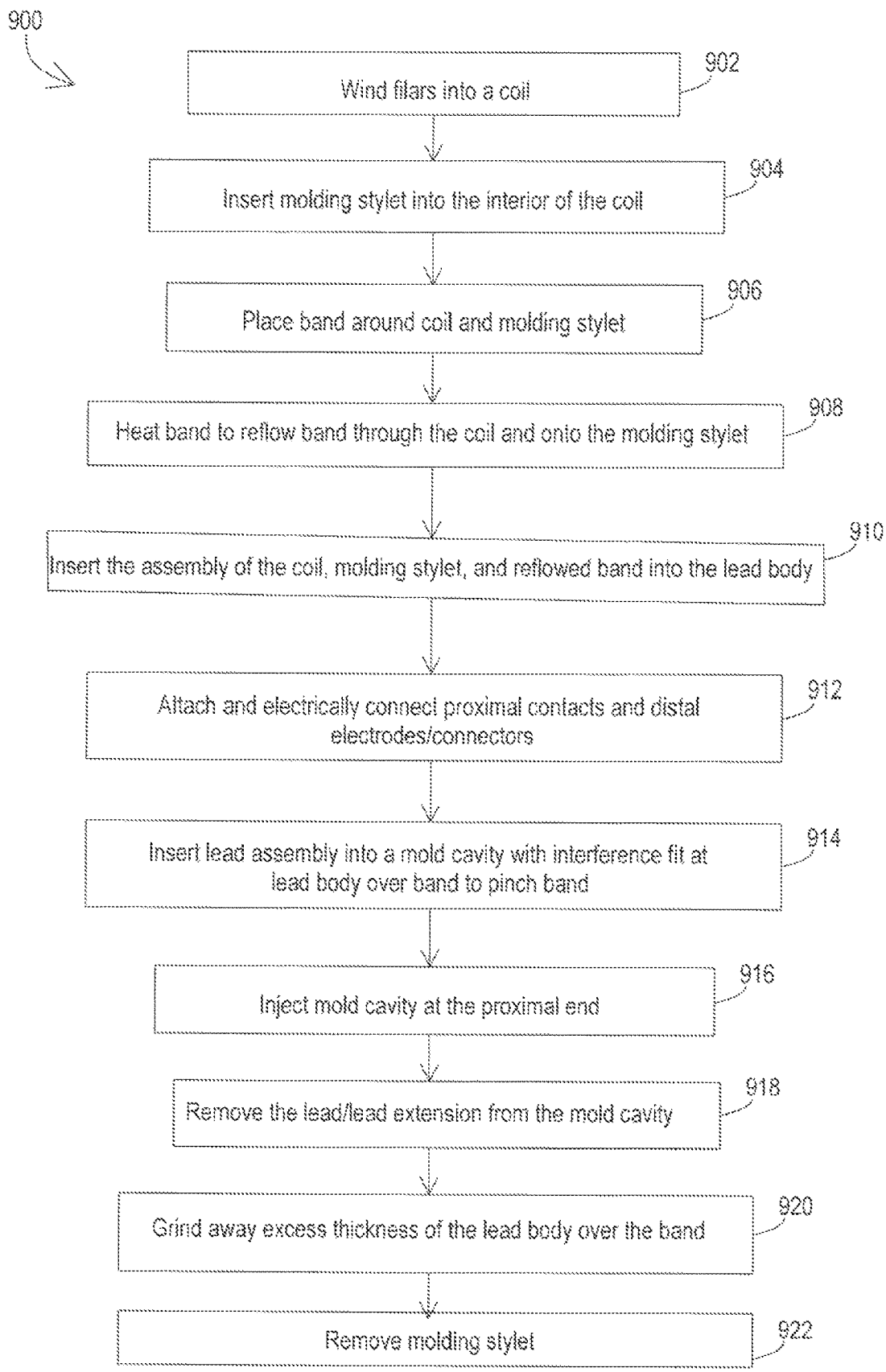
FIG. 9 shows manufacturing steps that may be taken to manufacture an example of an implantable medical lead or lead extension that includes the band.

FIG. 9 shows an example of a process for creating the implantable medical lead and/or lead extension having no stiffener rod but forming the band 306 with the lumen for the implantation stylet. For the lead 110 or lead extension 107 example shown in FIGS. 7A, 7B and 8A, 8B where the conductors become coiled at the band 306, the process begins by the filar conductors being wound into a coil at an operation 902. A proximal portion 302 of the filar conductors may remain linear as discussed above. Furthermore, for examples where the conductors are not coiled, then the operation 902 is omitted.

Once the filar conductors are in the desired configuration, such as coiled via operation 902, in this example the molding stylet 704 is inserted into the interior of the proximal end of the coil at an operation 904. For examples where the filar conductors are linear in the area where the molding stylet 704 is to be positioned, the proximal areas of the filars are positioned in linear fashion about the molding stylet 704. In either case, the molding stylet 704 is surrounded by the filar conductors. As an alternative, operation 904 may be omitted and in that case the coil remains on a mandrel used when coiling the conductors in operation 902.

At this point the band 306 that has not yet been reflowed is placed around the filar conductors and molding stylet 704 or mandrel at an operation 906. The band 306 is positioned at the desired axial location of the molding stylet 704 or mandrel and conductors. In the example of FIGS. 7A, 7B and 8A, 8B, the band 306 is placed such that a proximal end of the band is positioned on the filar conductors at the point where the filar conductors begin to coil such that the portion 310 of the conductors that are being encapsulated are fully coiled within the band 306.

Once the band 306 is positioned as desired, the band 306 is heated to reflow the band onto the portion 310 of the filar conductors and molding stylet 704 or mandrel at an operation 908. This reflow or melting of the band 306 causes the band 306 to encapsulate the portion 310 of the filar conductors and also contact but not bond to the molding stylet 704. This creates a configuration that adequately seals the lumen of the band 306 during injection molding but still allows for removal of the molding stylet 704. As noted, the molding stylet 704 may be coated with a material such as polytetrafluoroethylene (PTFE) that prevents bonding of the band 306.

The assembly of the filar conductors, band 306, and molding stylet 704 if previously installed may then be inserted into the empty tubular lumen 312 of the lead body 112 at an operation 910. The molding stylet 704 may be placed into the lumen 312 at this point, replacing the mandrel, if not previously installed. The lumen 312 of the lead body 112 is large enough to receive the coiled conductors 308 without restriction. The lumen 312 of the lead body 112 is also large enough to receive the reflowed band 306, although the reflowed band 306 may have an interference fit within the lumen 312. Once inserted, the filar conductors extend distally so that the distal end is in position to connect to where distal electrodes of the lead, or distal connectors of the lead extension, will be while the proximal end of the filar conductors is in position to connect to where the proximal contacts will be.

The proximal contacts and distal electrodes, or distal connectors of a distal lead bore for a lead extension, may be attached to the lead body, if not already present thereon, and then electrically connected to the filar conductors at an operation 912. This electrical connection may be done in the typical manner for implantable medical leads and/or lead extensions where the filar conductor is directed through an aperture in the lead body to the corresponding proximal contact or distal electrode or distal connector, and then a weld or other electrically conductive bond is formed.

At this point, the proximal lumen 312 of the lead body 112 that contains the linear proximal ends 302 of the filar conductors remains open. Therefore, in this example, the proximal end is completed by filling the proximal lumen 312 with injection molding material. To accomplish this, the proximal end of the lead 110 and/or lead extension 107 is inserted into a mold cavity at an operation 914. An example of the mold cavity 602 is again shown in FIG. 10A where the lead 110 or lead extension 107 has been inserted for purposes of injection molding of the proximal end of the outer circumference lumen 312.

In this example, the mold cavity 602 is provided with an annular protrusion 604. The lead body 112 of this example also has the annular protrusion 111 where the lead body is thicker and thus has a larger diameter than the remainder of the lead body 112. The protrusion 604 is brought into contact with the protrusion 111 via an interference fit due to the protrusion 111 having a contact surface with a diameter greater than the diameter of the contact surface of the protrusion 604. Thus, the protrusion 604 creates radially inward pressure at the protrusion 111 as also occurred for the prior embodiments that include the stiffener rod. This radially inward pressure causes the lead body 112 to pinch tightly against the reflowed band 306, which creates a seal 606. It will be appreciated that an annular protrusion 604 of the mold cavity 602 may be sized to apply radially inward pressure onto the lead body 112 in the area of the band 306 without the lead body 112 including the annular protrusion 111. However, the annular protrusion 604 may create a degree of damage to the outer surface of the lead body where the radially inward pressure is applied, so including the annular protrusion 111 on the lead body 112 allows the damaged area to be removed by removal of the annular protrusion 111 as further discussed below.

The outer circumference of the proximal lumen 312 that surrounds the molding stylet 704 is then filled with injection material, such as polyurethane, at an operation 916. This reduces the size of the lumen 312 to isolate the conductors and the connections to the proximal contacts while adding stiffness in the proximal area where the contacts are located. Because the band 306 creates a seal together with the lead body 112 and molding stylet 704, the injection molding material is blocked from proceeding past the band 306. Therefore, the coiled conductors 308 distal of the band 306 are not encapsulated or otherwise constrained by the injection molded material, and the lead 110 and/or lead extension 107 retains flexibility distally of the band 306.

Once the injection molding is complete, the lead 110 and/or lead extension 107 is removed from the mold cavity at an operation 918. However, the protrusion 111 of this example remains on the lead body 112. Therefore, in this example, the excess thickness of the lead body 112 forming the protrusion 111 is ground away at an operation 920. The grinding of this example results in the lead body 112 having a same diameter at the area where the band 306 is located and adjacent areas. It will be appreciated that the grinding may result in a different diameter than the adjacent areas. As discussed above, the annular protrusion 111 may be damaged on the surface due to the mold protrusion 604 and grinding away the annular protrusion 111 thereby removes the damaged area, exposing the undamaged lead body beneath the protrusion 111. It will also be appreciated that the area of the lead body 112 damaged by the mold protrusion 604 may be left as is, such as for examples where there is no annular protrusion 111 during the injection molding process.

At this point, or prior to the grinding at operation 920, the molding stylet 704 may be removed from the proximal end of the lead 110 or lead extension 107 by pulling the molding stylet 704 proximally relative to the lead body 112 at an operation 922. The resulting lead 110 and/or lead extension 107 is thereby provided with the band 306 which encapsulates the conductors and while providing the stylet lumen 312 through the band 306 to allow for ingress and egress of the implantation stylet.

FIG. 7AA shows an alternative configuration of a lead 110 and/or lead extension 107 where there is no stiffener rod but there is a stylet tube 705. The stylet tube 704 provides the lumen 312 as can be seen in FIG. 8BB. The stylet tube 705 may be constructed of a material such as a biocompatible non-conductor, for instance polyurethane and the like. The molding stylet 704 may be placed in the lumen 312 provided by the stylet tube 705. Thus, in FIG. 7AA, it is the stylet tube 705 that is visible rather than the molding stylet 704. The molding stylet 704 can be seen within the lumen 312 of the stylet tube 705 in FIG. 8AA.

As can be seen in FIGS. 8AA and 8BB, the stylet tube 705 extends from the proximal end of the lead body 112 distally and passes through the lumen of the band 306. As the stylet tube 705 allows a stylet to easily pass through the coiled conductors 308, the stylet tube 705 may extend to the distal end of the lead or lead extension.

Figure 10A:
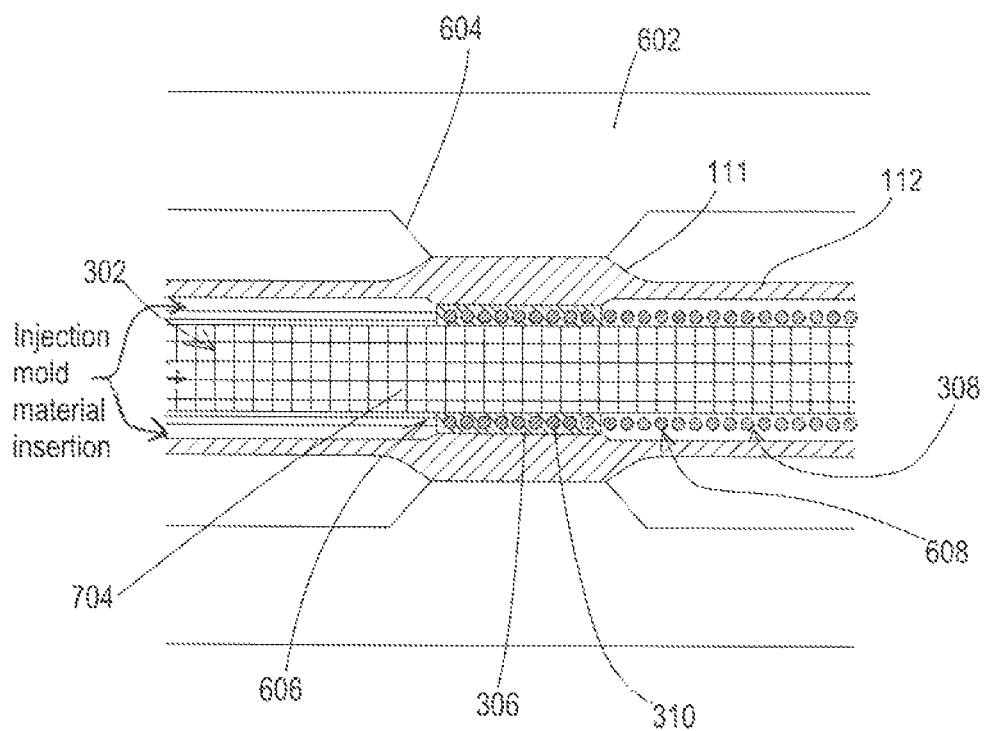
FIG. 10A shows a cross-sectional view of a mold cavity and implantable medical lead including a molding stylet or lead extension positioned within the mold cavity when injection molding a proximal end lumen of the implantable medical lead or lead extension.
Figure 10B:
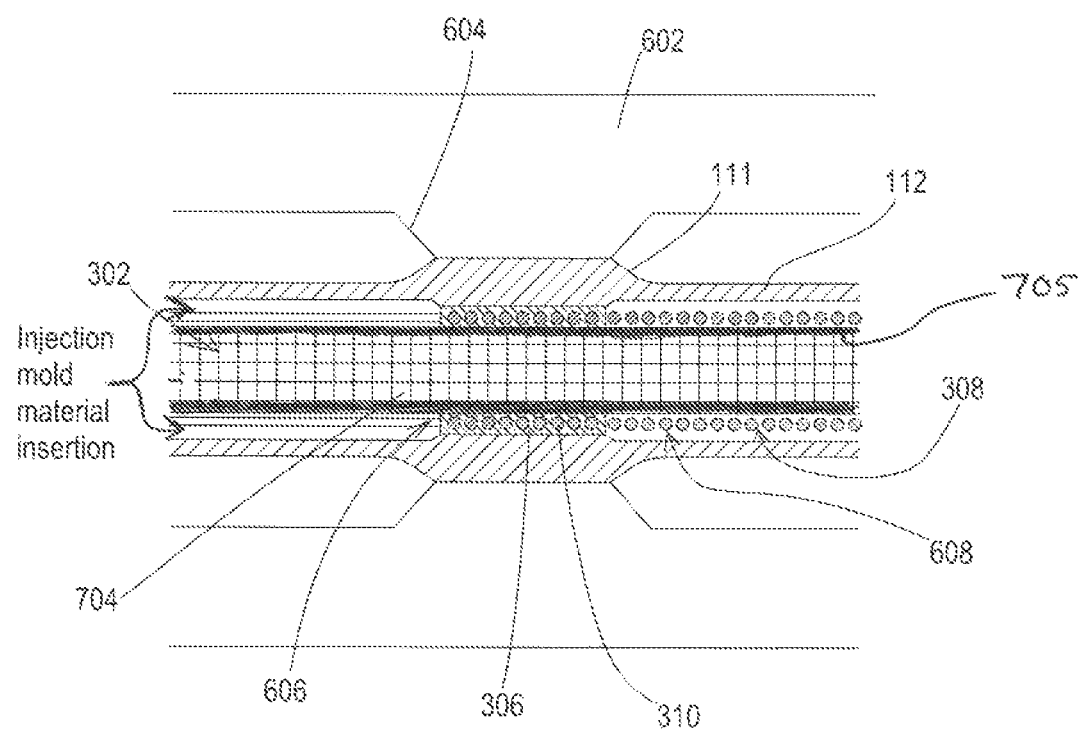
FIG. 10B shows a cross-sectional view of a mold cavity and implantable medical lead including a stylet tube and a molding stylet positioned within the mold cavity when injection molding a proximal end lumen of the implantable medical lead or lead extension.

The band 306 may be created by reflowing onto and bonding to the stylet tube 705 in the same manner discussed above in relation to the band 306 reflowing and bonding onto the stiffener rod of the prior embodiment. This effectively locks the band 306 and stylet tube 705 together. Additionally, this bonding of the band 306 to the stylet tube 705 allows a combination of the lead body 112, band 306, stylet tube 705, and molding stylet 704 to form a seal when injection molding the proximal end of the lead 110 or lead extension 107. FIG. 10B shows this injection molding configuration where the stylet tube 705 is present and is included in creating the seal to block the injection molding material from passing beyond the proximal end of the band 306.

Referring back to FIG. 9, when the stylet tube 705 is present, there may be slight differences in the operations. At operation 902, the filars may be wound into a coil directly on the stylet tube 705 that is on the mandrel rather than the filars being wound directly onto the mandrel. Additionally, at operation 908, the reflow of the band 306 causes the band to flow through the coil and onto the stylet tube 705 rather than onto the molding stylet 704 or mandrel. Thus, the reflowed band 306 may then bond to the stylet tube 705. At the operation 910, the assembly being inserted into the lead body 112 includes the stylet tube 705. At the operation 914, the assembly being inserted into the mold cavity includes the stylet tube 705. Thus, once the operations are completed the lead 110 or lead extension 107 includes the stylet tube 705 and is ready for implantation by passing an implantation stylet through the lumen 312 provided by the stylet tube 705.

While embodiments have been particularly shown and described, it will be understood by those skilled in the art that various other changes in the form and details may be made therein without departing from the spirit and scope of the invention.

What is claimed is:

1. An implantable medical apparatus, comprising:
   a lead body having a proximal end and a distal end, the lead body defining a lumen;
   a proximal contact on the lead body in proximity to the proximal end;
   a distal element coupled to the lead body in proximity to the distal end;
   a conductor electrically coupled to the proximal contact and the distal element, the conductor extending through the lumen;
   a stiffening element present within the lumen; and
   a non-conductive band present within the lumen and surrounding the stiffening element, the nonconductive band encapsulating a portion of the conductor and being bonded to the stiffening element.

2. The implantable medical apparatus of claim 1, wherein the conductor forms a coil and wherein the stiffening element is present within an interior of the coil.

3. The implantable medical apparatus of claim 1, wherein the non-conductive band comprises a reflowed polymer.

4. The implantable medical apparatus of claim 3, wherein the bond is produced by the reflowed polymer contacting the stiffening element.

5. The implantable medical apparatus of claim 3, wherein the reflowed polymer comprises a reflowed polyurethane.

6. The implantable medical apparatus of claim 3, wherein the reflowed polymer has a durometer Shore hardness of 80A.

7. The implantable medical apparatus of claim 1, wherein the stiffening element comprises a polyurethane.

8. The implantable medical apparatus of claim 1, wherein the stiffening element comprises one of a stylet tube or a molding stylet, and wherein the stiffening element extends to the distal end of the lead body.

9. The implantable medical apparatus of claim 1, where the distal element comprises a distal electrode.

10. The implantable medical apparatus of claim 1, wherein the distal element comprises a distal connector.

11. The implantable medical apparatus of claim 1, wherein the stiffening element comprises at least one of a stiffener rod, a stylet tube, or a molding stylet.

12. The implantable medical apparatus of claim 11, wherein the stiffening element comprises the stiffener rod, and wherein the stiffener rod has a durometer Shore hardness of 75 D.

13. An implantable medical system, comprising:
   an implantable medical device;
   an implantable medical apparatus coupled to the implantable medical device, the implantable medical apparatus comprising:
   a lead body having a proximal end and a distal end, the lead body defining a lumen;
   a proximal contact on the lead body in proximity to the proximal end;
   a distal element coupled to the lead body in proximity to the distal end;
   a conductor electrically coupled to the proximal contact and the distal element, the conductor extending through the lumen;
   a stiffening element present within the lumen; and
   a non-conductive band present within the lumen and surrounding the stiffening element, the nonconductive band encapsulating a portion of the conductor and being bonded to the stiffening element.

14. The implantable medical system of claim 13, wherein the conductor forms a coil and wherein the stiffening element is present within an interior of the coil.

15. The implantable medical system of claim 13, wherein the non-conductive band comprises a reflowed polymer.

16. The implantable medical system of claim 15, wherein the bond is produced by the reflowed polymer contacting the stiffening element.

17. The implantable medical system of claim 15, wherein the reflowed polymer comprises a reflowed polyurethane.

18. The implantable medical system of claim 15, wherein the reflowed polymer has a durometer Shore hardness of 80A.

19. The implantable medical system of claim 13, wherein the stiffening element comprises a polyurethane.

20. The implantable medical system of claim 13, wherein the stiffening element comprises one of a stylet tube or a molding stylet, and wherein the stiffening element extends to the distal end of the lead body.

21. The implantable medical system of claim 13, wherein the implantable medical apparatus comprises an implantable medical lead and the distal element comprises a distal electrode.

22. The implantable medical system of claim 13, wherein the stiffening element comprises at least one of a stiffener rod, a stylet tube, or a molding stylet.

23. A method of constructing an implantable medical apparatus, comprising:
   placing a stiffening element near a proximal end of a conductor;
   placing a non-conductive band about the stiffening element and a portion of the conductor;
   reflowing the non-conductive band to encapsulate the portion of the conductor and to bond to the stiffening element;
   surrounding the conductor, the stiffening element, and the conductor with a lead body;
   attaching a proximal contact in proximity to a proximal end of the lead body and electrically connecting the proximal contact to the conductor; and
   coupling a distal element to the distal end of the lead body and electrically connecting the distal element to the conductor.

24. The method of claim 23, wherein the stiffening element comprises at least one of a stiffener rod, a stylet tube, or a molding stylet.

* * * * *